United States Patent
Struys et al.

(10) Patent No.: US 6,599,281 B1
(45) Date of Patent: Jul. 29, 2003

(54) SYSTEM AND METHOD FOR ADAPTIVE DRUG DELIVERY

(75) Inventors: Michel Struys, Belsele (BE); Tom De Smet, Temse (BE); Linda Versichelen, Afsnee (BE)

(73) Assignee: Aspect Medical Systems, Inc., Newton, MA (US)

( * ) Notice: Subject to any disclaimer, the term of this patent is extended or adjusted under 35 U.S.C. 154(b) by 0 days.

(21) Appl. No.: 09/564,292

(22) Filed: May 3, 2000

(51) Int. Cl.[7] .............................................. A61M 31/00
(52) U.S. Cl. ...................................................... 604/503
(58) Field of Search ........................ 604/65–67, 30–34, 604/303

(56) References Cited

U.S. PATENT DOCUMENTS

| | | |
|---|---|---|
| 4,741,732 A | 5/1988 | Crankshaw et al. |
| 5,496,537 A | 3/1996 | Henry |
| 5,665,065 A * | 9/1997 | Colman et al. ............. 604/131 |
| 5,813,397 A | 9/1998 | Goodman et al. |
| 6,016,444 A | 1/2000 | Roy |
| 6,042,579 A | 3/2000 | Elsberry et al. |
| 6,053,887 A | 4/2000 | Jordan et al. |

FOREIGN PATENT DOCUMENTS

| | | | |
|---|---|---|---|
| WO | WO 93 14807 | 8/1993 | |
| WO | WO 98 50095 A | 11/1998 | |
| WO | WO 00 67820 A | 11/2000 | |

* cited by examiner

Primary Examiner—Teresa Walberg
Assistant Examiner—Vinod D. Patel
(74) Attorney, Agent, or Firm—Hale and Dorr LLP

(57) ABSTRACT

A system and method for controlling the administration of medication to a patient utilizes adaptive feedback to achieve and maintain a target effect in said patient. A sensor package having one or more sensors is used to sense an attribute of the patient and to provide a parameter indicating the attribute being sensed. A medication delivery controller accepts one or more parameters from the sensor package and uses these parameters to determine the effect of a medication on a patient and the concentration level of medication that will achieve a desired effect. The medication delivery controller controls the medication delivery unit to deliver the medication at a rate determined to achieve said target concentration level of said medication in said patient. If the patient's response to a given medication changes as a result of external stimuli, the medication delivery controller can detect this change and determine a new concentration level of medication which will achieve the desired effect. The medication delivery controller can steer the medication delivery unit to administer an amount of medication to reach this new concentration level.

13 Claims, 9 Drawing Sheets

SYSTEM AND METHOD FOR ADAPTIVE DRUG DELIVERY

BACKGROUND OF THE INVENTION

1. Field of the Invention

The present invention relates generally to the administration of medication, and more particularly to a closed loop system and method for adaptively controlling the administration of medication.

2. Related Art

Intravenous drug administration is a well-known and commonly used technique for administering medication to a patient. Intravenous administration of a medication results in a blood concentration of the medication in a patient with the object of obtaining a desired effect on that patient. An appreciation of the interrelationship between drug dose, concentration, effect and time is fundamental in pharmacology. Such an appreciation can be gained by understanding a Pharmacokinetic-Pharmacodynamic (PK-PD) model. This model characterizes concentration, effect and dosage by analyzing the pharmacokinetic impact of the drug dose and then the pharmacodynamic effect the drug dose has on the patient.

Specifically, pharmacokinetics (PK) seeks to describe, understand and predict the time-course of drug concentration (usually in the blood); it quantifies the relationship between dose and concentration. Pharmacodynamics (PD) seeks to describe the time-course and magnitude of the physiological effect of that concentration; it quantifies the relationship between concentration and effect. Hence, the marriage of kinetics and dynamics provides insight into the time-course of drug effect, and forms a basis for optimizing and controlling drug dosage.

One concern associated with controlling the dose/effect relationship of medication arises from the accuracy of the drug effect measurement. Another concern arises from the fact that other factors can come into play, altering the dose/effect relationship for a patient. These concerns apply to medication in general and particularly to anesthetic drugs.

Because different anesthetic drugs have different effects and side effects, drug effect can be measured in different ways. At present there are a variety of clinical indicators used as the basis for the administration of drugs to achieve a specific anesthetic state. According to conventional wisdom the depth of anesthesia and anesthetic drug effect is clinically judged by the observation of somatic (patient movement) and autonomic (increased heart rate and blood pressure, tearing and pupil dilatation) reflexes. There are, however, case reports of awareness during surgery in unparalyzed patients in whom somatic reflexes were absent. Even though these cases are relatively rare, the occurrences indicate that the observation of spontaneous movement during surgery is not foolproof.

If muscle relaxants are also present in the patient in doses that prohibit movement, adequacy of anesthesia is most often assessed by the observation of autonomic reflexes, although a relationship to awareness has not been established. Another confounding factor is that anesthetic effect may be modified by disease, drugs and surgical techniques. Further, the degree of interpatient variability in the dose/effect relationship of anesthetic agents is high. In actual clinical practice, opiates and other drugs may be added to anesthetic making the clinical evaluation of anesthetic depth even more difficult.

Another conventional measure of anesthetic depth and anesthetic drug effect is the electroencephalography (EEG). However, because changes in EEG morphology are profound and also different for each type of anesthetic being administered, interpretation of subtle changes in the raw (unprocessed) EEG requires a trained electroencephalographer and thus is typically not done on line during anesthesia and sedation. For this reason, computer processing of the EEG is often employed to compress the large amount of information present in the raw EEG, while preserving the information relevant to the monitoring application.

Several EEG monitors have been designed for use in the operating room, intensive care unit and other settings. These devices perform data compression and produce trends of frequency content, amplitude, and asymmetry between channels. Two main approaches have been used for this purpose: Fourier Analysis and Bispectral Analysis.

The Fourier analysis approach represents a complex waveform as a summation of sine waves of different frequencies and amplitudes. The power spectrum can be computed from a Fast Fourier Transform (FFT) analysis. The power spectrum is in turn used to calculate a number of descriptive parameters such as the spectral edge frequency (frequency below which 95% of the power spectrum (SEF 95%) or 50% of the power (median frequency or MF) exists). These measures of the EEG are often used in anesthetic pharmacological research. However, the use of power spectrum EEG analysis during clinical anesthesia has been limited for several reasons. First, different drugs have different effects on these power spectral measures. Also, at low concentrations these drugs induce activation, but at higher concentrations the drugs cause EEG slowing, even introducing iso-electric EEG episodes, referred to as burst suppression. Thus, both low and high concentrations can cause a non-monotonic relationship between the power spectral measures and the patient's clinical state.

Bispectral analysis is a quantitative EEG analysis technique that has been developed for use during anesthesia. Bispectral analysis of EEG measures consistency of phase and power relationships among the various frequencies of the EEG. The Bispectral Index® developed by Aspect Medical Systems, Inc., which is derived from bispectral analysis of the EEG, is a single composite EEG measure that tracks EEG changes associated with the different anesthetic states.

Principles of pharmacokinetics have recently been used to develop various schemes of computerized infusion for intravenous anesthetics and sedative drugs. A computer is provided with mean population pharmacokinetic data for the drug to be used, including the desired plasma concentration. The computer then calculates the quantity of drug and the rate of infusion for a desired ("target") concentration; an infusion pump then delivers the required infusion rate and volume to achieve that target concentration.

These problems of drug administration are not limited to anesthetic drugs, nor are they limited to intravenous delivery of medication. In clinical practice, there is no ideal plasma-concentration to produce a certain drug effect. The specific concentration required depends on factors such as individual pharmacological variability, the interaction with other simultaneously used drugs and the intensity of the surgical stimulus.

SUMMARY OF THE INVENTION

The present invention provides a system and method for determining and maintaining a desired concentration level of medication in a patient to achieve and maintain a desired effect on that patient. Generally speaking, in accordance with one embodiment of the invention, a medication delivery controller uses a patient response profile to determine a concentration of medication in the patient that will achieve the desired effect on the patient. Using this information, the medication delivery controller provides instructions to a medication delivery unit such as, for example, an infusion pump or inhalation device, to deliver the medication to the patient at a rate that will achieve the desired concentration level of the medication in the patient.

The effect of the medication on the patient is monitored to determine whether the patient response profile has changed. If the patient's response profile has changed, the medication delivery controller calculates a new patient response profile and uses this new patient response profile to determine a new concentration level of medication which will achieve the desired effect on the patient.

In one example application of the invention, the medication delivery controller can be implemented to determine a desired concentration level of an anesthetic medication to provide a desired level of sedation for a patient. However, the invention can be implemented with any of a variety of different medications to determine and maintain a concentration level of medication that will result in the desired effect on the patient.

In one embodiment, a sensor package having one or more sensors can be included to sense one or more attributes of the patient. These attributes can include one or more conditions of the patient, which are used in determining the effect of the medication on the patient. The sensor package provides parameters quantifying these attributes to the medication delivery controller. For example, in the case of anesthetic drugs, attributes useful in determining the level of sedation of the patient can include the patient's electroencephalogram (EEG), as well as other attributes such as the patient's heart rate, blood pressure, and oxygen saturation. Parameters quantifying these attributes such as, for example, the Bispectral Index of the patient's EEG can be determined and provided to the medication delivery controller. The medication delivery controller utilizes these parameters to determine the level of sedation of the patient. Likewise, other attributes and their associated parameters can be used to measure or otherwise quantify the effect of other types of medications on a patient.

The medication delivery controller utilizes one or more parameters from the sensor package to determine the effect of the medication on the patient. In one embodiment, these parameters can be used to determine an initial patient response profile defining the patient's individualized response to the medication. In operation, the parameters can be used to determine whether the patient's response to the medication has changed as a result of external stimuli. If the patient's response to the medication has changed, the medication delivery controller can determine the new response profile. From this new response profile, the medication delivery controller can determine a new concentration level of the medication that will achieve the desired effect on the patient. Based on the patient response profiles determined for the patient, the medication delivery controller instructs a medication delivery unit to deliver the medication to the patient at the desired rate or level to achieve the determined concentration.

An advantage of the invention is that changes in a patient's response to a medication can be determined using information obtained from the sensor package. With this information, delivery parameters of the medication such as, for example, the infusion rate, can be adjusted to ensure that the desired effect on the patient is achieved and maintained. As a result of this adaptive feedback process, a desired effect of a medication on a patient can be automatically maintained even if the patient's response to the medication changes as a result of external stimuli.

Further features and advantages of the invention as well as the structure and operation of various embodiments of the invention are described in detail below with reference to the accompanying drawings.

BRIEF DESCRIPTION OF THE DRAWINGS

The present invention will be described with reference to the accompanying drawings. In the drawings, like reference numbers indicate identical or functionally similar elements. Additionally, the left-most digit(s) of a reference number identifies the drawing in which the reference number first appears.

FIG. 5, which comprises

DETAILED DESCRIPTION OF THE INVENTION

1. Overview of the Invention

The present invention is directed toward a system and method for controlling the delivery of medication using an adaptive feedback control system. According to one embodiment of the invention, the patient's response profile to a medication is determined. The response profile can, in one embodiment, be measured as the effect the medication has on the patient at various concentration levels. Once the response profile is determined, the patient is provided with a level of that medication to achieve the desired effect. The patient is monitored to determine whether the desired effect is maintained. Provided the desired effect is achieved at the administered concentration, no changes in medication level are required.

However, should external stimuli affect the patient's response profile, the administered concentration no longer maintains the desired effect. As such, a new response profile is determined, and the concentration adjusted to achieve the desired effect. External stimuli which may affect the patient's response profile can include, for example, surgical manipulations, additional medications administered to the patient, patient activities, the passage of time or other occurrences which may alter the effect a medication has on the patient.

2. Example Environment

The invention can be implemented in any medication delivery environment where it is desired or required to achieve a predetermined effect, even where external stimuli may affect the dose/effect relationship. One such example environment is the intravenous infusion of anesthetic medication to a patient to achieve a desired depth of anesthesia. The invention is from time to time described herein in terms of this example environment. Description in these terms is provided for ease of discussion only. After reading this description, it will become apparent to one of ordinary skill in the art that the present invention can be implemented in any of a number of different medication delivery environments where it is desirable to monitor or adjust the delivery of medication to achieve a desired result.

3. Controlled Feedback Drug Delivery

Figure 1:
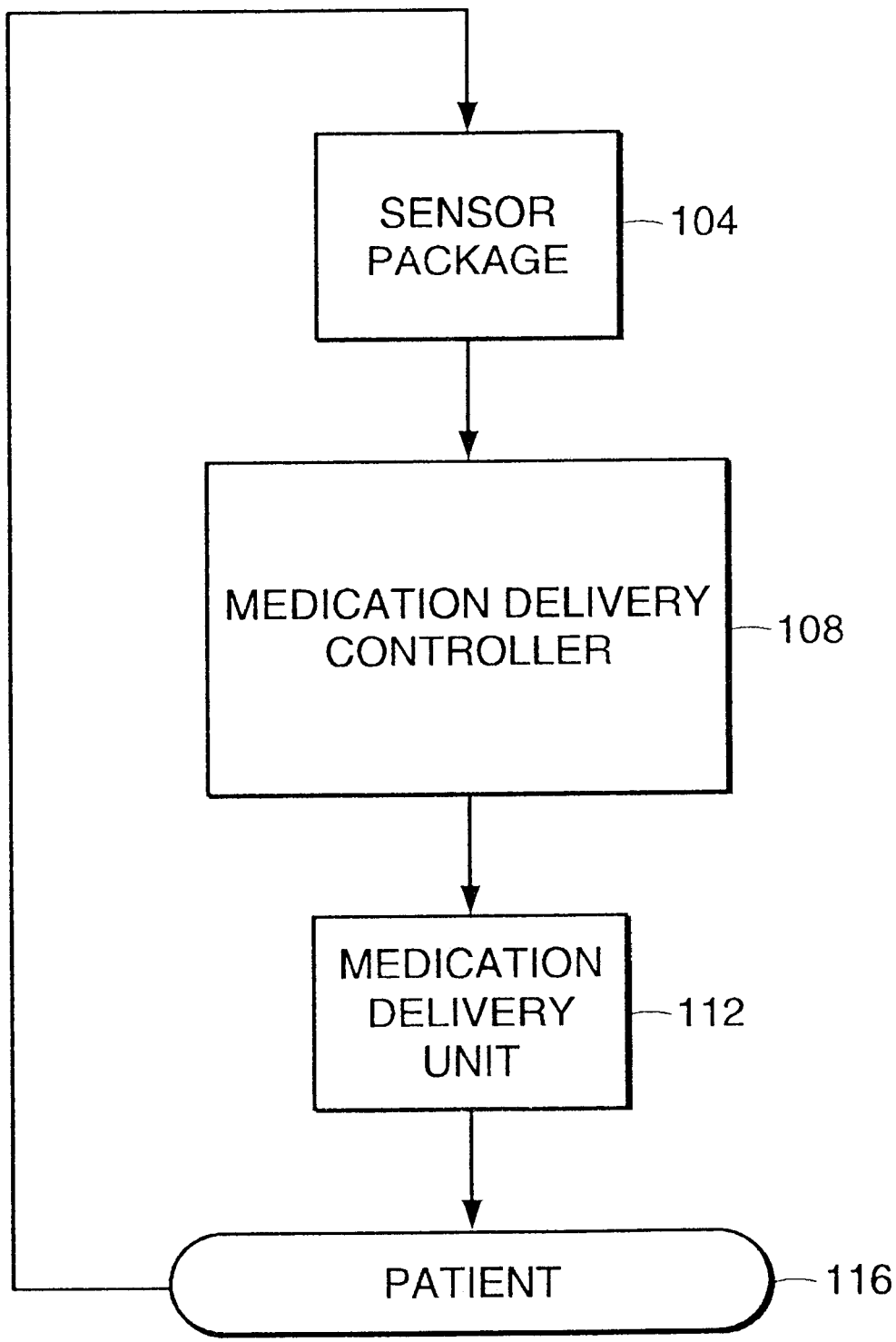
FIG. 1 is a block diagram illustrating a sensor package, medication delivery controller, and medication delivery unit in accordance with one embodiment of the invention.

FIG. 1 is a block diagram generally illustrating an application of a medication delivery controller in accordance with one embodiment of the invention. A patient 116 under surgical care, intensive care or other related healthcare is monitored by a sensor package 104 to determine the patient's response to a delivered medication. Sensor package 104 can include one or more sensors to sense the condition of or attributes of the patient. Sensor package 104 can provide parameters such as, for example, patient blood pressure, heart rate, temperature, EEG parameters, EKG parameters or other parameters representing the patient's overall condition or representing specific attributes about the patient.

Medication delivery controller 108 accepts the one or more parameters and utilizes these parameters to determine the desired concentration level of a medication. Medication delivery controller 108 controls medication delivery unit 112 to administer medication to patient 116 at the desired rate or interval to achieve the desired concentration of medication in the patient's blood stream. Medication delivery controller 108 controls medication delivery unit 112 such that the concentration of medication in the patient's blood stream is either maintained, increased, or decreased. Decisions to maintain or adjust the rate or interval of medication delivery are made based on an evaluation of the parameters received from sensor package 104.

Medication delivery unit 112 receives instructions from medication delivery controller 108 to adjust the rate or interval at which medication is delivered. Medication delivery unit 112 can be implemented as an infusion pump, inhalation device, or other medication delivery device. For example, in the case of an infusion pump, the medication delivery controller can adjust the infusion rate of medication delivery unit 112 to achieve a higher or lower blood level concentration of the subject medication in patient 116.

Figure 2:
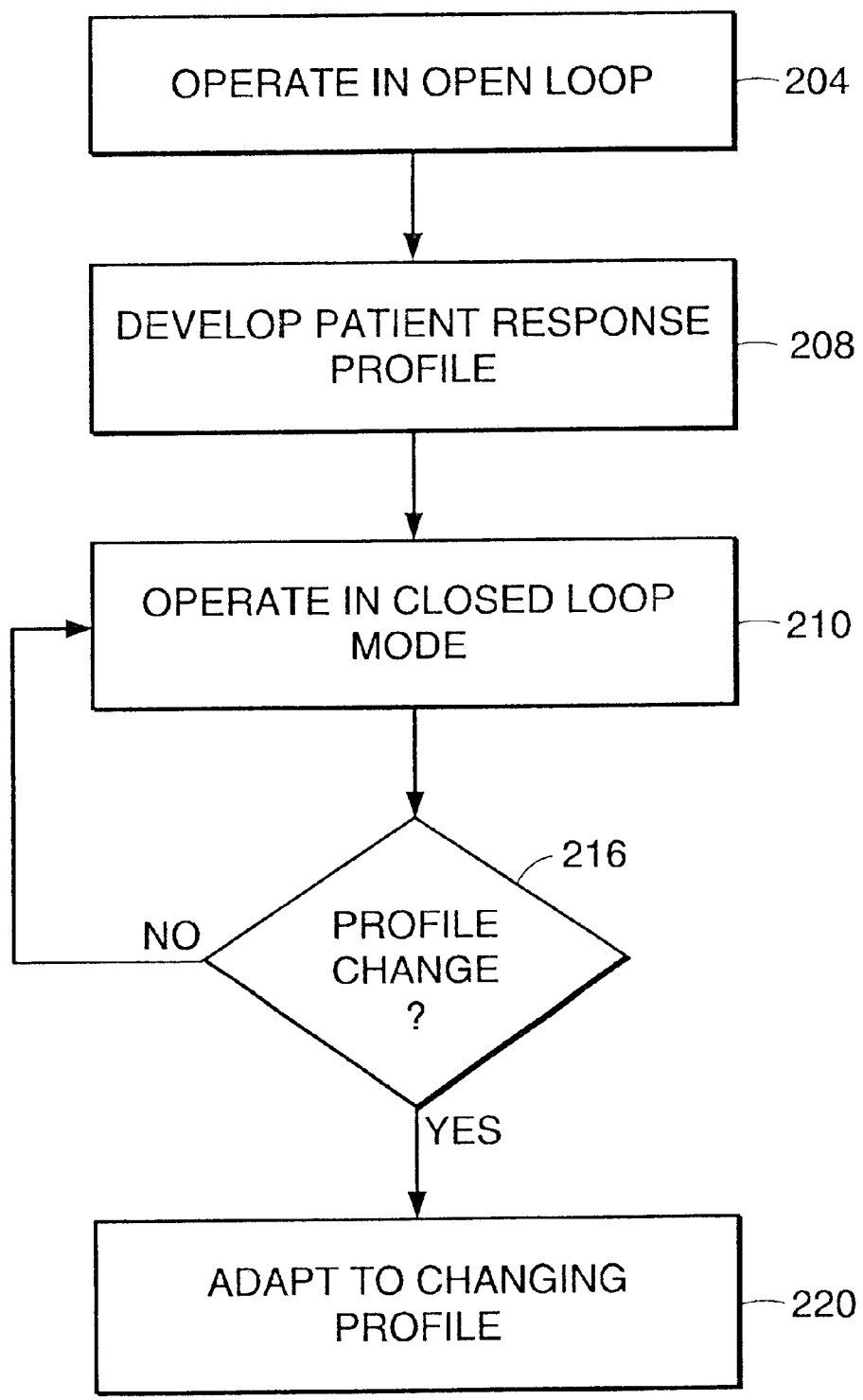
FIG. 2 is an operational flow diagram illustrating the process of adapting to a changing patient response profile in accordance with one embodiment of the invention.

FIG. 2 is an operational flow diagram illustrating the operation of medication delivery controller 108 according to one embodiment of the invention. In a step 204, medication delivery controller 108 operates in an open loop mode, preferably without reference to the parameters from sensor package 104. In this open-loop mode, medication delivery controller 108 controls medication delivery unit 112, such that varying concentrations of medication are delivered to patient 116.

In a step 208, a patient response curve, or response profile, is developed as a result of the open-loop operation. More particularly, results from sensor package 104 are used to track the effect of the medication on patient 116 at varying concentration levels.

Once the patient response profile is determined, medication delivery controller 108 operates in the closed-loop mode as illustrated by step 210. In the closed-loop mode, medication delivery controller 108 evaluates one or more parameters received from sensor package 104 to ensure that the desired effect on patient 116 is achieved. Because of external stimuli such as, for example, additional medication, surgical or invasive procedures, changing patient condition, or other factors affecting patient 116, the patient response profile may be altered. That is, the external stimuli may cause a patient to respond differently to a given concentration of medication. As such, in a closed-loop mode, medication delivery controller 108 monitors the parameters received from sensor package 104 to determine whether the patient response profile has changed.

Provided the patient response profile has not changed, medication delivery controller 108 continues to operate in the closed-loop mode and maintains the current blood concentration level of the medication. Steps 216 and 210 illustrate this. If, on the other hand, medication delivery controller 108 senses a change in the patient response profile, medication delivery controller 108 determines the new medication concentration level required to maintain a desired effect on the patient. If, for example, a higher concentration of medication is required to achieve or maintain a desired effect on the patient, medication delivery controller 108 instructs medication delivery unit 112 to adjust the rate at which the medication is administered to the patient. For example, where medication delivery unit 112 is an infusion pump, medication delivery controller 108 may instruct medication delivery unit 112 to increase the infusion rate, thereby increasing the concentration of medication in the patient's blood stream. The steps of sensing a change in the patient response profile and adapting to the sensed change is illustrated by steps 216 and 220.

Figure 3:
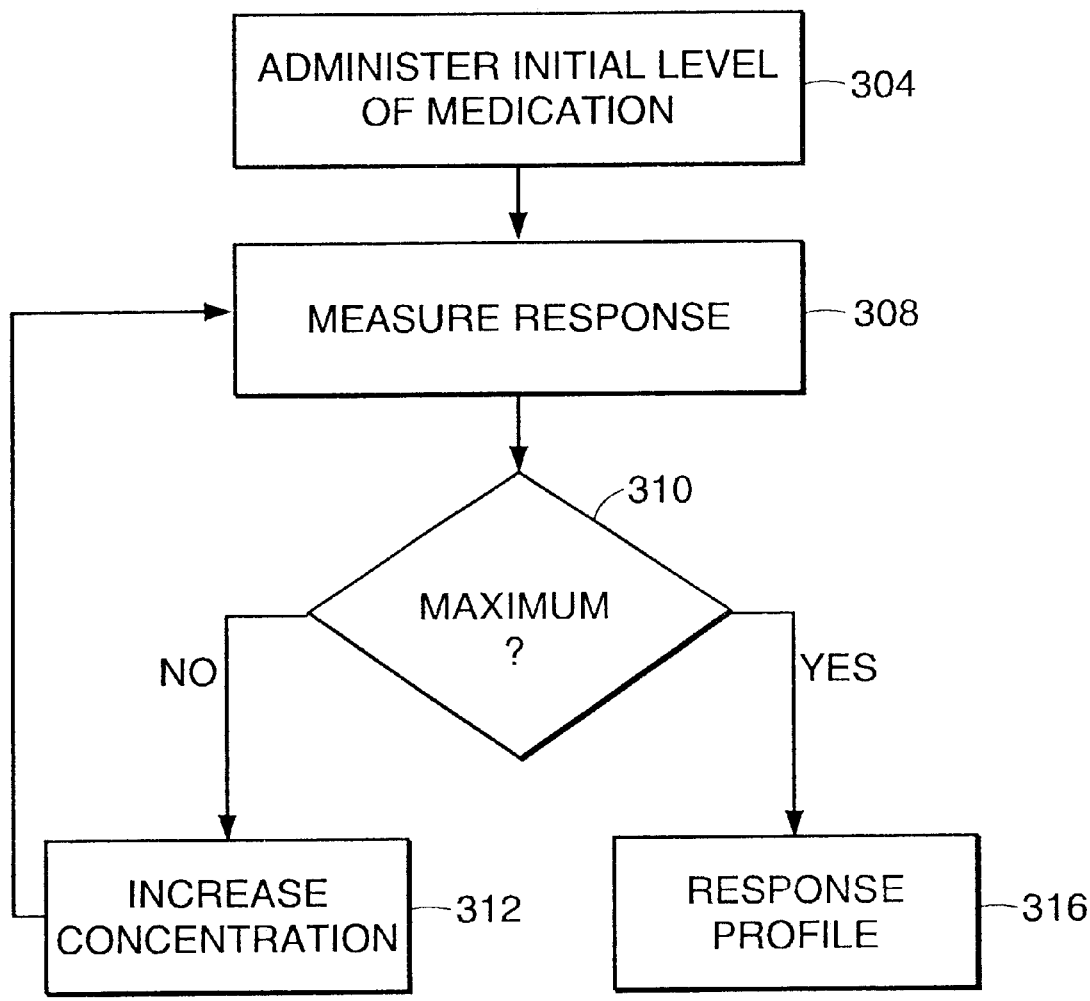
FIG. 3 is an operational flow diagram illustrating a process for determining an initial patient response profile in accordance with one embodiment of the invention.

As stated above, before operating in the closed loop mode it is preferable that a patient response profile is determined. For some medications, it is possible that pre-determined profiles could be provided. These predetermined profiles may be adjusted based on patient attributes such as height, weight, gender, etc. However, for most medications and especially for anesthetics, the effect of the medication on the patient is highly individualized. For these medications, it is desirable to determine the patient's specific, or individualized, response profile to the medication. FIG. 3 is an operational flow diagram illustrating one technique for determining a patient response profile according to one embodiment of the invention. In a step 304, in initial level of medication is administered to the patient. This initial level achieves an initial concentration of medication in the patient's blood stream.

In a step 308, the effect of this initial concentration is measured. In the embodiment illustrated in FIG. 1, the effect of the medication is measured by sensor package 104. Sensor package 104 provides parameters to medication delivery controller 108 that can be used to determine or quantify the effect of the medication on patient 116.

In a step 312, the concentration of medication is increased and the effect of this increased concentration is measured in step 308. Preferably, the increase in concentration provided in step 312 is a stepwise increase allowing the effect of specific or quantifiable concentration levels on patient 116 to be measured.

The process of increasing the concentration and measuring the effect of the increased concentration on the patient is repeated until a final concentration level is achieved. This is illustrated by decision step 310. It should be noted that the final concentration level used for the determination in step 310 is preferably a final concentration level required to develop a relatively accurate patient response profile. It is typically not necessary, and more than likely not desirable, that this final concentration level be the maximum level of medication that can be infused into patient 116.

In a step 316, the measured effects at the various concentration levels are plotted to form the patient response profile. Interpolation and extrapolation can be used to create a complete curve from the obtained data points. Knowledge about the effects of the medication in general can be used for the interpolation and extrapolation. Such knowledge is particularly useful for extrapolation at the maximum concentration levels in the patient.

Figure 4:
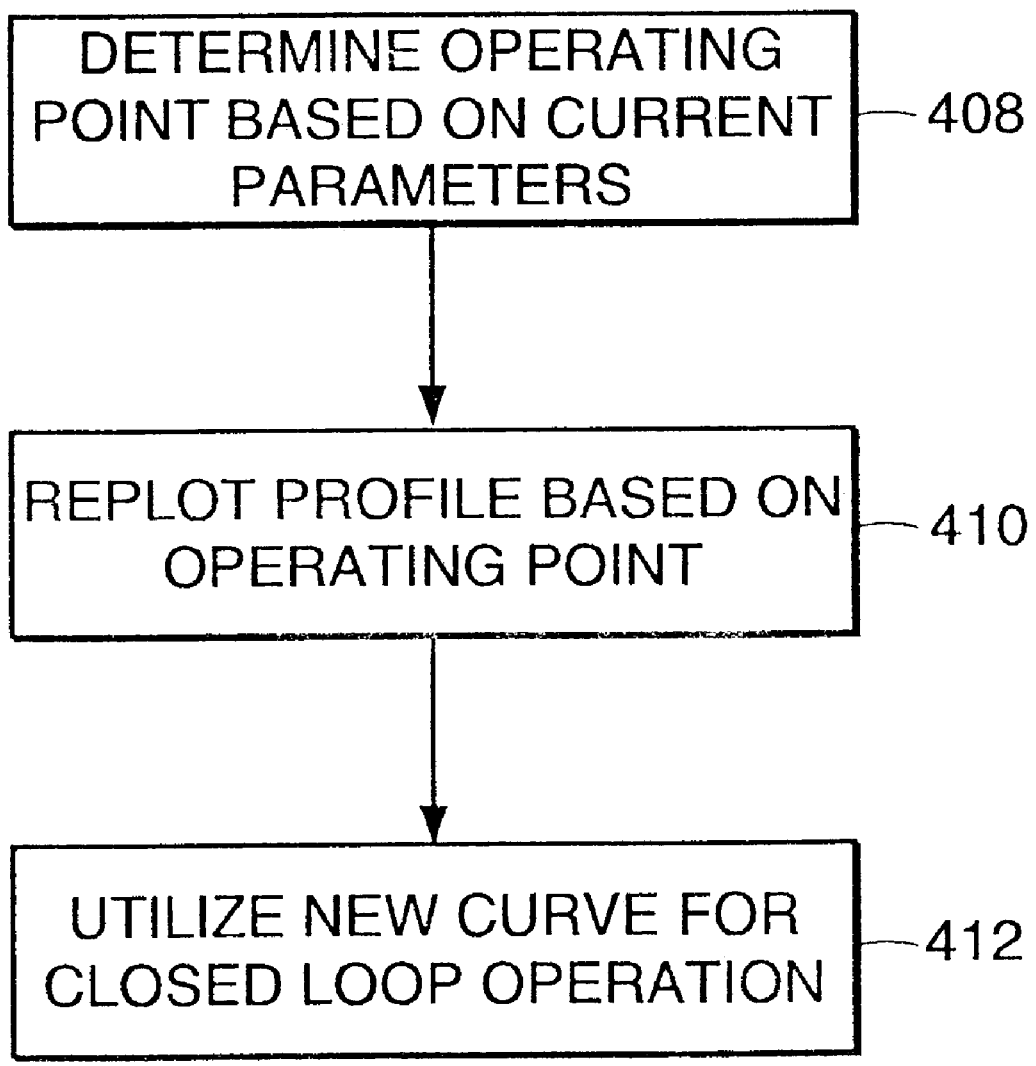
FIG. 4 is an operational flow diagram illustrating a method for determining a new patient response profile in accordance with one embodiment of the invention.

As stated above, in step 220 medication delivery controller 108 adapts to a changing profile to insure that the desired effect is achieved on patient 116. FIG. 4 is an operational flow diagram generally illustrating a process by which this adaptation to a changing profile can be performed in accordance with one embodiment of the invention. In a step 408, medication delivery controller 108 determines a first operating point based on current parameters. Specifically, in one embodiment, the current operating point is a level of medication delivery that results in a desired concentration level calculated to achieve the desired effect on patient 116 based on the patient response profile. As the patient response profile changes, in step 410 the response profile is replotted based on a current operating point. Specifically, in one embodiment, the previously determined response profile is shifted such that it intersects the new operating point. Applications of this embodiment are described in more detail below with reference to FIG. 5.

In a step 412, the newly plotted response profile is used by medication delivery controller 108 to ensure that the appropriate concentration of medication is provided to patient 116 by medication delivery unit 112 to achieve the desired effect on patient 116.

Figure 5A:
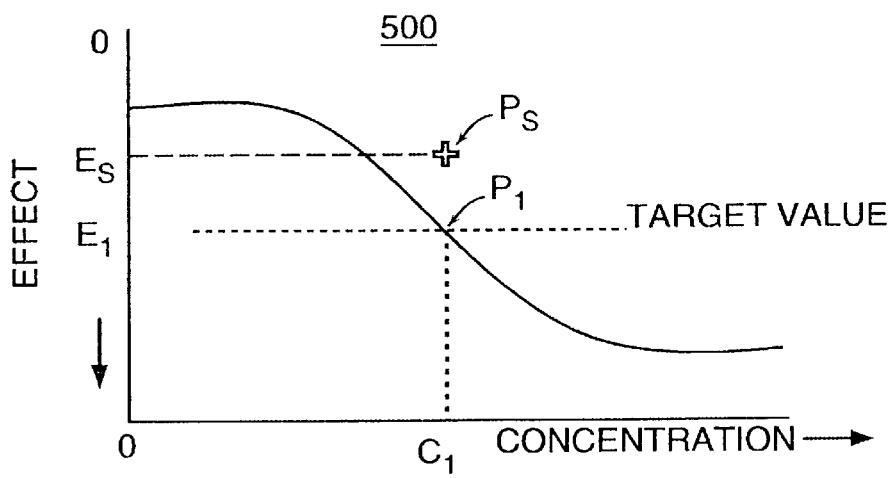
FIGS. 5A, 5B and 5C, is a diagram illustrating a patient response profile and the shifting of the patient response profile to determine a new patient response profile.
Figure 5B:
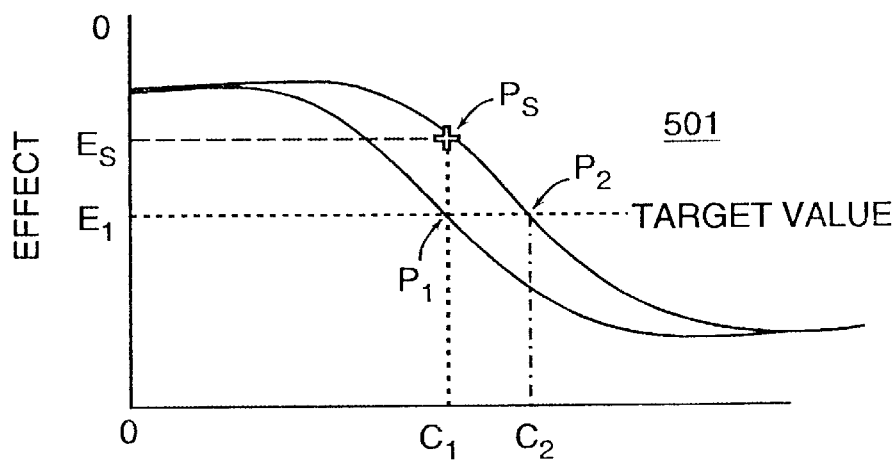
Figure 5C:
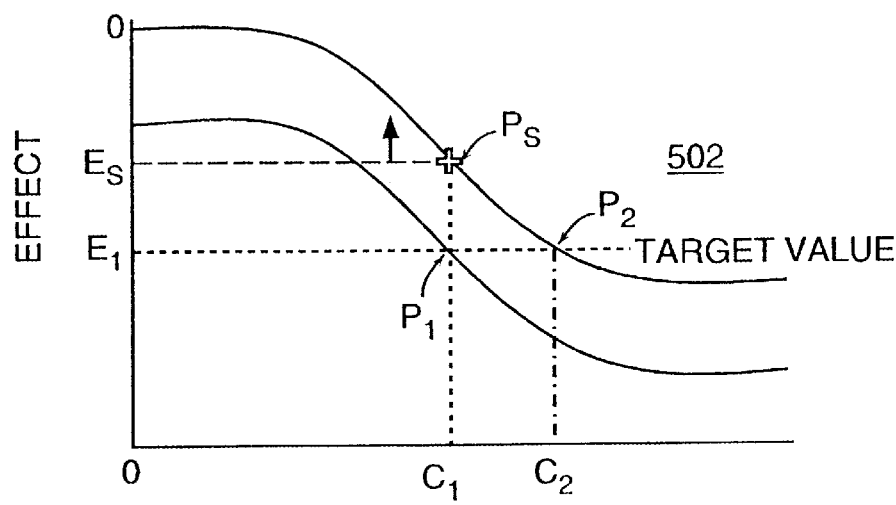

FIG. 5, which comprises FIGS. 5A, 5B and 5C, illustrates an example patient response profile 500 and the shifting of patient response profile 500 as a result of a change in the patient's response to a specific new situation. FIG. 5A illustrates an example patient response profile 500 plotted as the effect of the medication on patient 116 versus the concentration of medication at the effect site of patient 116. FIG. 5A illustrates that for a desired target effect $E_1$ on patient 116, there is a point $P_1$ on patient response profile 500 for which there is a corresponding level of concentration $C_1$ of medication in the patient.

As stated above, external stimuli may trigger such a change in patient response profile 500. Some examples of such external stimuli may include an additional medication administered to the patient; a physical activity such as surgical stimulus, change in environment, or other physical stimulus; or some other external stimuli. To look at just one example, consider a situation in which a surgical stimulus is applied to the patient. As a result of this surgical stimulus, the effect of the original medication concentration $C_1$ on patient 116 is diminished. This example is illustrated by the point $P_S$ on FIG. 5A at which for a concentration level $C_1$ the measured effect of the concentration level of medication on a patient is diminished to $E_S$ and is, as clearly illustrated, no longer on patient response profile 500. Therefore, to determine a new concentration level of the medication required to achieve the desired effect $E_1$ on the patient, a new patient response profile 500 is calculated. However, calculation of a new patient response profile 500 in the open-loop mode may not be practical or possible. Therefore, the new operating point $P_S$ is used as a starting point for redrawing patient response profile 500 in a shifted position.

For example, FIG. 5B illustrates the shifting of the patient response profile 500 horizontally until the shifted patient response profile intersects the operating point $P_S$. The intersection of the new profile 501 with the target effect value $E_1$, as illustrated by point $P_2$, is used to calculate the new concentration of medication $C_2$ required to achieve the desired effect $E_1$. Although the profile is illustrated in this example as shifting to the right, it should be understood that the profile could shift either right or left, depending on the reaction to the stimulus.

Alternatively, patient response profile 500 can be shifted vertically in either direction to intersect the new measured operating point $P_s$. The projection of the crossing point $P_2$ of the new profile 502 and the target value $E_1$ onto the concentration axis provides the new desired concentration $C_2$ to reach the target value $E_1$. As would be apparent to one of ordinary skill in the art after reading this description, patient response profile 500 could also be shifted in both the X and the Y directions to intersect the new operating point $P_s$.

4. Embodiments of the Invention in Anesthetic Drug Applications

As described above, one application of the invention is in the environment of the delivery of an anesthetic to achieve a desired level of sedation, or sedation effect, on a patient. One or more embodiments of the invention are now described in terms of this example environment. There are a number of parameters that can be used individually or in combination to monitor the effects of an anesthetic drug on a patient. One parameter, known as the Bispectral Index can be used to measure the hypnotic effect of an anesthetic on cerebral activity.

As such, in one embodiment of the invention, a bispectral analysis of the patient's EEG signal is used as a method for monitoring the hypnotic effect of an anesthetic drug on the patient. The non-linear behavior of biological systems may tend to generate relationships between component sinusoids of signals such as the EEG. This phase-coupling information between different frequency bands of the EEG spectrum is typically ignored by normal power spectrum analysis. The bispectral analysis attempts to quantify the quadratic (second-order) non-random phase coupling that appears between the components of the EEG signal. This can give fundamental information about the system generating the signal and the influence of the inter-relations between different frequency components (phase coupling) and the non-stationary component of the human EEG signal.

Through the identification of predictive and correlative features in, among others, the EEG bispectrum and the time-domain level of burst suppression, a multi-variant parameter can be calculated referred to as the Bispectral Index. The Bispectral Index is a quantifiable parameter well known in the art. The Bispectral Index is described in U.S. Pat. No. 5,792,069 (which is incorporated herein by reference) and has been integrated into the bispectral EEG monitors such as those available from Aspect Medical Systems, Inc., of Natick, Mass., USA.

As such, the Bispectral Index is utilized by medication delivery controller 108 to determine whether the desired effect, i.e., level of sedation, has been achieved for a patient.

Because the combination of the EEG and hemodynamics may prove to be more adequate in monitoring the depth of anesthesia than a single parameter, both hemodynamics and the Bispectral Index can be used as parameters in the closed-loop system according to one embodiment of the invention. As stated above, it is often a goal of a medication delivery system to achieve and maintain a desired effect on the patient. This desired effect or level of effect can be referred to as the set point, or target value. The set point specified by the anesthetist or other health care professional is preferably approached and maintained as closely as possible during the maintenance of the anesthesia or sedation. Preferably, in one embodiment, set points for the different variables to be controlled can be offered to the health care professional as the values measured after induction, in a quiet state before intubation. The set points can be changed according to clinical needs during the course of the procedure or treatment of the patient.

Figure 6:
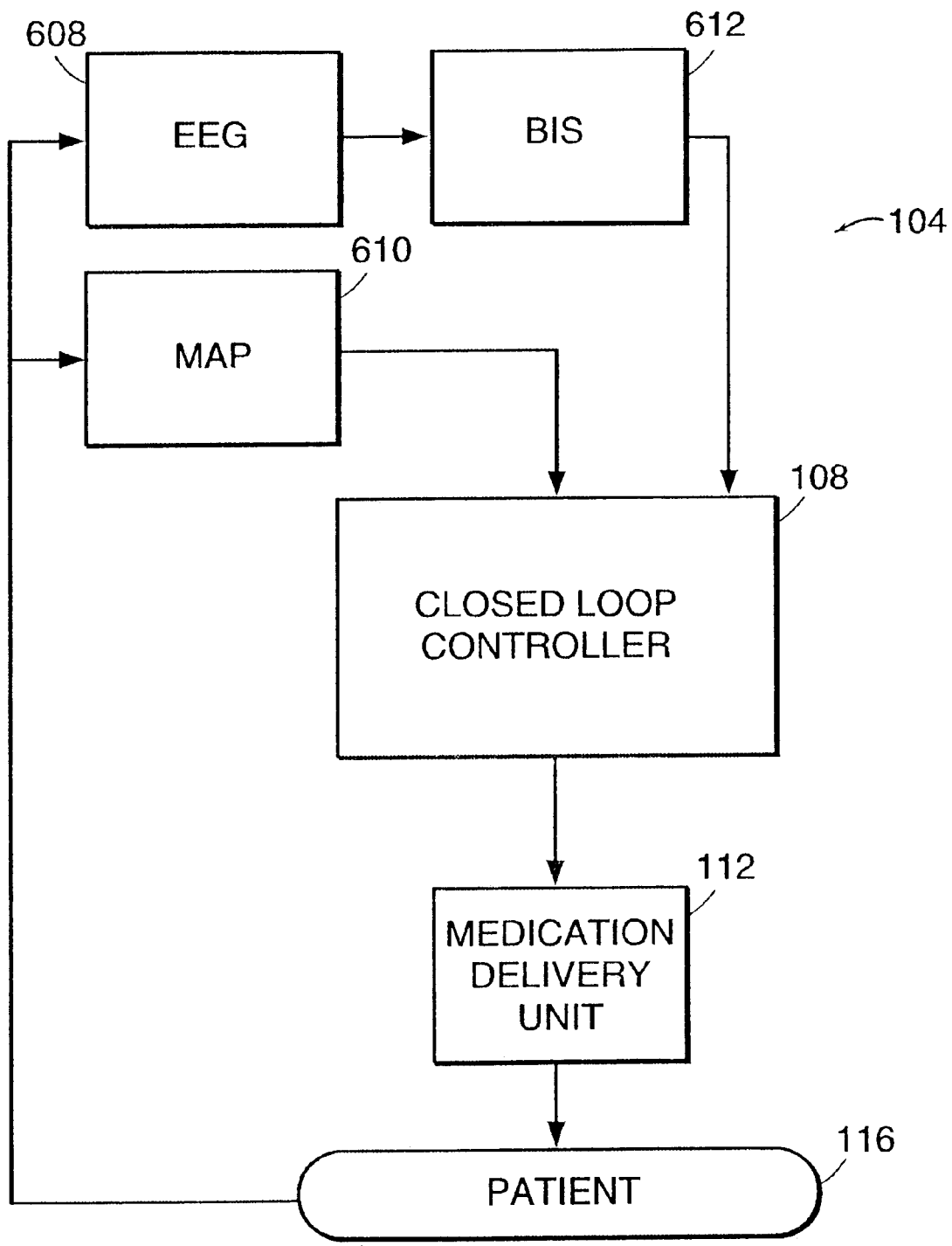
FIG. 6 is a block diagram illustrating an application of the invention suitable for use in the administration of anesthetic medications in accordance with one embodiment of the invention.

FIG. 6 is a block diagram illustrating an example implementation of a medication delivery controller 108 and an anesthetic drug delivery environment that utilizes mean arterial pressure and Bispectral Index as parameters in the closed-loop delivery system. Referring now to FIG. 6, as illustrated in this example embodiment, sensor package 104 includes an EEG monitor 608 and a Bispectral Index device 612. As illustrated in FIG. 6, patient 116 is connected to EEG monitoring device 608. Preferably, EEG monitoring device 608 is configured to accept EEG data and perform calculations to obtain processed EEG data. The processing can include a determination of a Bispectral Index, a suppression ratio, and artifact information. Sensor package 104 also includes a measurement device 610 for determining mean arterial pressure that is also provided to medication delivery controller 108. These parameters can be provided to medication delivery controller 108 via a hardwired or wireless communications interface such as, for example, an RS-232 interface and are used as correlates of drug effects. The Bispectral Index is used as a controlled variable while, in one embodiment, the suppression ratio and artifact information are used as safety parameters. In an alternative embodiment, other signals (EEG or EP) may be used as a controlled variable, as well as other processed parameters computed from these signals such as EEG spectral edge, median frequency and absolute and relative EEG power within various frequency bands.

Figure 7:
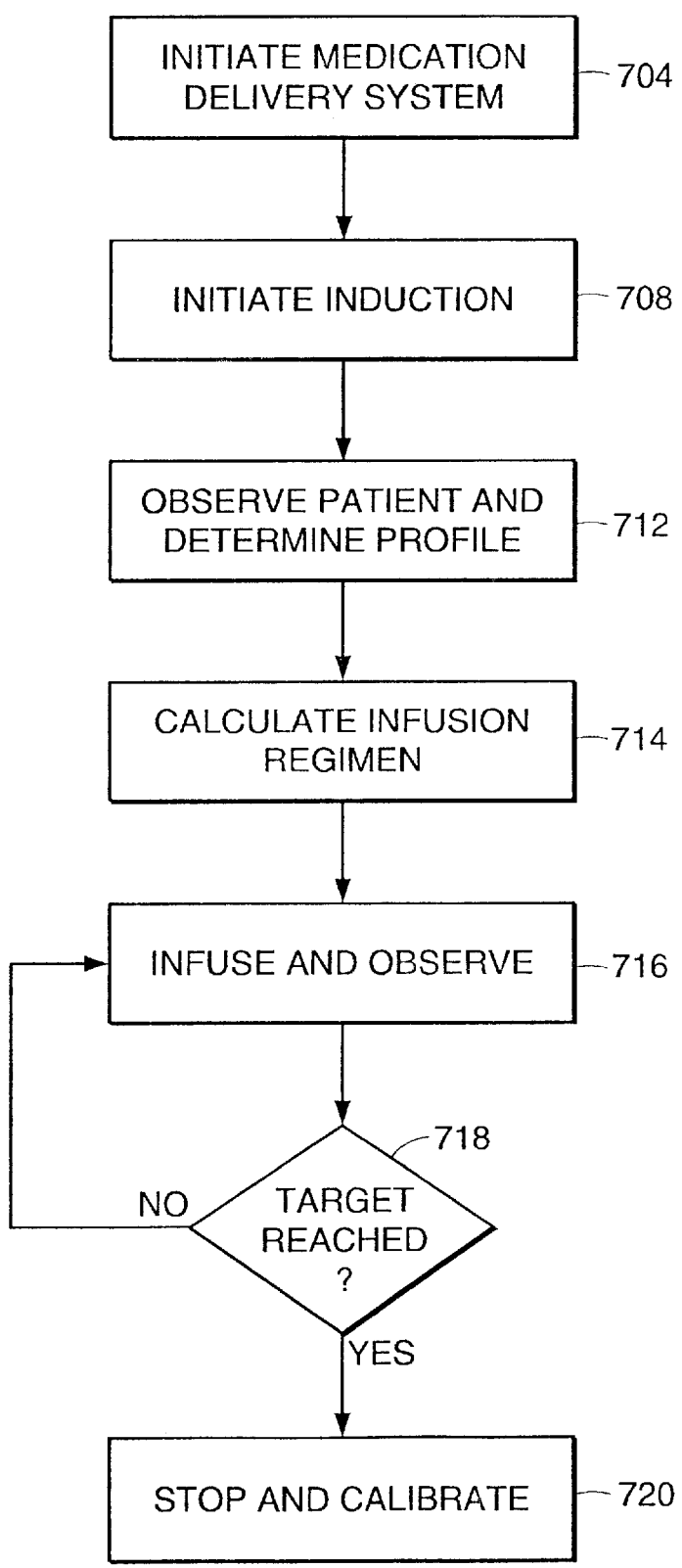
FIG. 7 is an operational flow diagram illustrating the operation of a medication delivery controller in the example environment of the administration of anesthetic medication in accordance with one embodiment of the invention.

FIG. 7 is an operational flow diagram illustrating the operation of medication delivery controller 108 in this example environment in accordance with one embodiment of the invention. In a step 704, the medication delivery system is initiated. Preferably, in this step, patient individual anthropometric data, such as, for example, weight, age, height and gender are entered. Additionally, at this step, the target Bispectral Index and safety values (e.g., suppression ratio limit, MAP, etc.) can be entered. Preferably, the system is initiated prior to induction of the patient. Additionally, the anesthetist sets the initial effect-site concentration. The anesthetist or other clinician can enter this initial data by a manual entry using a user-interface as described in more detail below. Additionally, this data can be entered by a communications interface, such as, for example, by local area network or other communications, provided this information is available for retrieval by this medium.

In a step 708, the process of induction is initiated. In a step 712, during the induction, medication delivery controller 108 observes the patient's behavior to a specific effect-site concentration of the anesthetic. This observation is performed to enable the medication delivery controller 108 to calculate the patient's individual response profile. In the case of an anesthetic drug, the response profile is, in one embodiment, a pharmacodynamic Hill curve. Specifically, in one embodiment, medication delivery controller 108 initiates an induction at a specific effect-site concentration of anesthetic that is preferably set by the anesthetist. This concentration is increased automatically at periodic intervals with predefined steps. For example, in one embodiment, the concentration is automatically increased every minute with a stepwise increase of 0.5 micrograms/milliliter. This step is referred to as effect-site controlled open-loop drug delivery using population pharmacokinetic modeling. Pharmacokinetic modeling is well known in the anesthesia art. Because large pharmacodynamic variability among patients can cause error when using a combined pharmacokinetic-pharmacodynamic model, the preferred embodiment utilizes an individualized Hill curve in adjusting the delivery of the anesthetic drug. Additionally, using mean population pharmacokinetic as well as mean population pharmacodynamic values for a particular dosage regimen in an individual patient may result in significant dosage error. The probability of this error occurring can be minimized or at least reduced by utilizing individualized Hill curves to adjust the delivery of the anesthetic drug.

In a step 714, medication delivery controller 108 calculates an infusion regimen to reach the specified effect-site concentration. The infusion regimen, which can be calculated in terms of a bolus and a maintenance infusion, can be specified in ml/hour used to steer medication delivery unit 112 in the delivery of medication to patient 116. During infusion, medication delivery controller 108 observes the parameters. If the target Bispectral Index is reached, the increase in effect-site concentration is stopped and controller 108 automatically calculates the Hill curve. Thereafter, medication delivery controller 108 switches automatically from open-loop control to closed-loop control. Steps 718 and 720 illustrate this.

In a closed-loop operation, medication delivery controller 108 operates in the adaptive closed-loop mode, shifting the Hill curve if required to change the concentration to achieve the desired level of sedation with patient 116.

5. Medication Delivery Controllers

Medication delivery controller 108 can be implemented utilizing a variety of different technologies in a variety of different architectures to achieve the desired result. As stated above, a primary purpose of a medication delivery controller 108 is to sense the resultant effect on patient 116 by the parameters from sensor package 104 and to adjust the medication delivery rate to achieve the desired result. Preferably, a processor-based software-controlled device is utilized to perform this function. The processor-based device includes an input interface to receive parameters from sensor package 104 and an output interface to provide control information to medication delivery unit 112.

Figure 8:
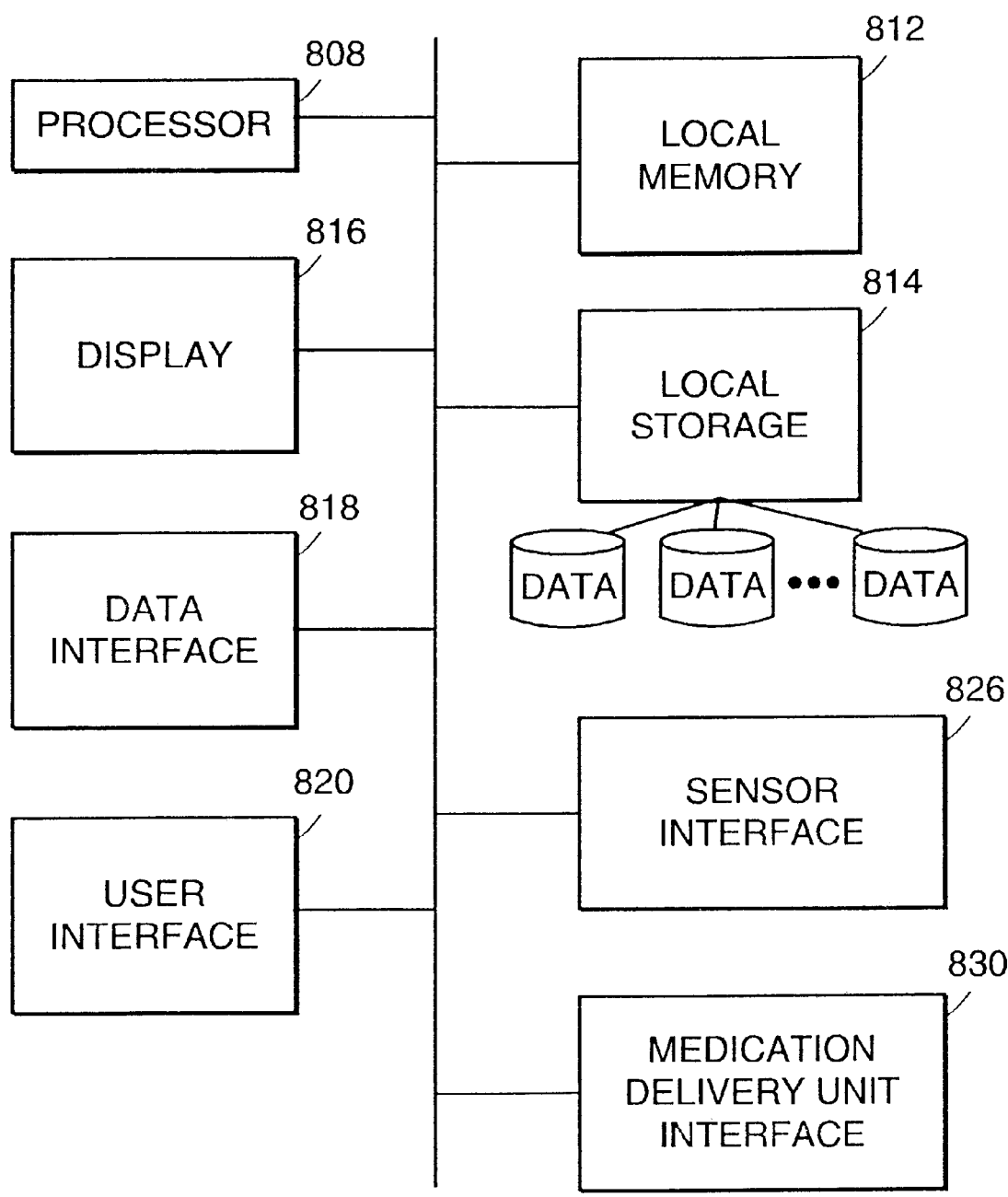
FIG. 8 is a block diagram illustrating an example architecture of a medication delivery controller in accordance with one embodiment of the invention.

As will be appreciated by one of ordinary skill in the art after reading this description, there are a number of devices and/or architectures that can be implemented to perform these functions. One such example architecture is illustrated in FIG. 8. The example architecture illustrated in FIG. 8 includes a processor 808, local memory 812, a sensor interface 826, and a medication delivery unit interface 830. Processor 808 can be implemented utilizing a variety of different processor types including, for example, the X86 family of processors or a Pentium® processor.

Local memory 812 can include random access memory (RAM) and read-only memory (ROM). Local memory 812 can be used to store program instructions that control processor 808, values or other variables used in operation of processor 808 in executing the program instructions, and results of the operation of medication delivery controller 108.

Sensor interface 826 and medication delivery unit interface 830 are included to provide interfaces to sensor package 104 and medication delivery unit 112, respectively. Interfaces 826, 830 can be implemented using hardwired or wireless interfaces. A variety of communications standards can be used such as, for example, RS-232, RS422, or any of a number of alternative communications standards or protocols.

Additionally, features can be included in the architecture of medication delivery unit 108 to provide enhanced or additional functionality. These additional features can include, for example, a display 816, a data interface 818, a user interface 820 and local storage. 814. Various embodiments of each of these additional components are now described. Display 816 can be included to provide information to anesthetist or other clinician utilizing medication delivery controller 108. Display 816 can be implemented using conventional technology and can be implemented as, for example, an LCD or a CRT display. Display 816 can be implemented as a simple text-only display providing the user with one or more lines of text informing the user of the Status or current operation being performed by medication delivery controller 108. Alternatively, display 816 can be implemented as a more conventional computer display offering text and graphics to the user such as that found on many Windows® based personal computers. In fact, in one embodiment, the software utilized to control medication delivery controller 108 is a software package designed to operate on the Windows® operating system. Display 816 can also be implemented as a touch-screen display to facilitate user input. Alternative display devices or configurations can also be used, depending on the application.

User interface 820 can be included to provide the user with a means for inputting user data to medication delivery controller 108. User interface can include, for example, a keyboard or keypad, a pointing device such as a mouse or other pointing device and an encoded label reader. Examples of an encoded label reader can include, for example, bar code label readers, magnetic stripe readers, OCR readers or other code reading devices. User interface 820 can be used by the clinician to provide data used by medication delivery controller 108 in its operation as well as to control or otherwise alter the operation of medication delivery controller 108. As stated above, an operator can enter patient attributes such as height, weight, age, and gender into medication delivery controller 108. User interface 820 can be provided to facilitate such entry.

A data interface 818 can also be included to allow medication delivery controller 108 to access data from or provide data to other entities or devices. For example, patient attributes or other data may be available to medication delivery controller 108 via an external database or other external source. Data interface 818 can be utilized as a conduit for providing this data to medication delivery controller 108. In one embodiment, data interface 818 can be implemented using a network interface to allow medication delivery controller 108 to provide information to or access information from one or more databases or other entities on a computer network. Data interface 818 can be implemented as a hard-wired or a wireless interface.

Preferably, medication delivery controller 108 is implemented as a fixed or transportable device rather than a portable device. Therefore medication delivery controller 108 is designed to be plugged into an A/C wall outlet. However, alternative embodiments can be implemented wherein medication delivery controller 108 is operated by batteries or other portable or transportable independent power source. Of course, the selection of components, especially, for example, the display, may be made based on power consumption and heat dissipation characteristics.

Additionally, a local storage device 814 can be included to provide storage for data or additional storage for program instructions. Local storage 814 can, for example, be implemented as a disk drive or other storage device. Local storage 814 can be used to store a variety of patient data or medication data as well as for storing a history of the operations performed by medication delivery controller 108.

As stated above, there are numerous alternative architectures that can be implemented to provide the functionality of medication delivery controller 108. The examples discussed above with reference to FIG. 8 are provided by way of example only. After reading this description it will become apparent to one of ordinary skill in the art how to implement medication delivery controller 108 using a number of alternative architectures and components.

As discussed, medication delivery controller 108 determines delivery parameters for the medication based on the response profile determined. In one embodiment, the delivery parameter determined is a required infusion rate. The infusion rate of a medication can be calculated by a straightforward mathematical formula based on the difference between the measured value and the chosen target value set by the user. Conventional controllers often operate without knowledge of the drug metabolism and the realized concentration values. Without fine-tuning for a specific situation, these conventional controllers can be slow to establish control and become dangerous to use because of possible oscillations. Furthermore, fine tuning of conventional controllers is difficult as the human body and its responses to medications is very complex. As a result, this may lead to clinical difficulties due to the complex pharmacologic behavior of products used, inter-individual pharmacologic variability and patient's reactions to external stimuli.

A model-based controller may be used to control the administration of drugs in response to clinical effects where the control is based on knowledge of the drug and its effect in the human body based on a mathematical model. In a preferred embodiment, a model-based adaptive controller is utilized which compares the output predicted by the model to actual output values in order to adjust the model parameters for the individual. According to a preferred embodiment of the invention, medication delivery controller 108 calculates a target concentration value for a TCI (Target Controlled Infusion) system that steers for this concentration by calculating the corresponding infusion regimen. Using a TCI system, the input-output complexity can be reduced. In other words, if the system can immediately steer the blood or effect-site concentration, instead of the pump rate, third order behavior of the anesthetic or other medication in the body does not have to be accounted for by medication delivery controller 108 because the TCI system compensates for this. Thus, this reduces the overall order of the system to be controlled giving a much faster result. Also, this provides an easy way of quickly checking the actions of medication delivery controller 108, as a particular blood or effect-site concentration of the drug can be easily related to a certain effect. Moreover, medication delivery controller 108 can be programmed to not go beyond certain dangerous conditions, such as dosage or duration of drug administration.

In one embodiment, the invention utilized RUGLOOP® as PK TCI program. The RUGLOOP program was written by Tom DeSmet and Michel Struys and is freely available on the Internet at http://pkpd.icon.palo-alto.med.va.gov/. Another embodiment uses STANPUMP as the PK TCI program; this program was written by Steven L. Shafer, M.D. of Stanford University, Anesthesiology Service (112A) PAVAC, 3801 Miranda Avenue, Palo Alto, Calif. 94304, and is freely available from the author. These TCI programs are capable of steering both blood and effect-site concentration. RUGLOOP is described in a thesis entitled "Ontwerp Van Een Computergestuurd closed-loop Anesthesiesysteem (Design of a Computer-Controlled Closed-Loop Anesthesia System)," filed at the Department of Electronics and Information Systems, Faculty of Applied Sciences, University of Gent, 1995. The algorithms in RUGLOOP are adapted from the STANPUMP Target-Controlled Infusion System, described in Shafer, S. L. and Gregg, K. M., "Algorithms to Rapidly Achieve and Maintain Stable Drug Effect with a Computer-Controlled Infusion Pump", J. Pharmaceouinetics Biopharm. 20(2):147–169 and Shafer, S. L., Siegel, L. C., Cooke, J. E. and Scott, J. C. "Testing Computer-Controlled Infusion Pumps by Simulation", Anesthesiology, 68:261–266, 1988. RUGLOOP is freely available from Aspect Medical Systems, Newton, Mass.

In one embodiment, effect-site compartment modeling can be applied to connect the pharmacokinetic part with the pharmacodynamic part. This is motivated by the observed hysteresis between measured blood/drug concentrations and any currently measured index of drug effect (e.g., processed EEG). This hysteresis between pharmacokinetic and pharmacodynamic can be quantified by a rate constant, $k_{e0}$, using the convolution $C_e = C^* k_{e0} e^{-k_{e0} t}$ (equation 0), where $C_e$ is the effect-site drug concentration and C is the plasma drug concentration. Values of $k_{e0}$ for various drugs are well known in the literature. The smaller the value of $k_{e0}$, the greater the temporal hysteresis between the central and the effect-site compartment concentrations. This time course of drug effect parallels the time course of the effect compartment modeling. Thus, it is desirable to control drug concentration in the effect compartment rather than the central compartment. Effect-compartment modeling is well known in the art and is described by Sheiner, et al., in *Simultaneous Modeling of Pharmacokinetics and Pharmacodynamics: Application to d-tubocurarine, Clin Pharmacol Ther,* 1979;25(3):358–71.

Pharmacodynamics describes the relationship between drug concentration and drug effect. A sigmoid $E_{max}$ pharmacodynamic model can characterize the relationship between steady-state plasma drug concentration, C, and drug effect E, which ranges from no effect, $E_0$, to the maximum effect, $E_{max}$. This model uses the downward-sloping Hill equation in which the effect E is quantified by mean arterial pressure and Bispectral Index:

$$E_0 - \frac{E_{max} \cdot C^\gamma}{C_{50}^\gamma + C^\gamma} \quad \text{or} \quad E = H(C) \tag{1}$$

where γ is a variable influencing the slope and sigmoidicity of the curve and $C_{50}$ is the steady-state plasma drug concentration producing half the maximum effect. As stated above, in one embodiment of the invention, an existing TCI system is utilized allowing the blood or effect-site concentration to be used as a variable influencing the effect to be controlled, whereas an alternative embodiment uses the pump rate. In the former, the necessary increase or decrease of the blood or effect-site concentration is derived using the inverse Hill curve of the variable to be controlled based on a knowledge of the effect-site concentration-effect relationship.

In one embodiment of the invention, medication delivery controller 108 can be made more robust by combining two identical controllers. One controller utilizes the Bispectral Index as the variable to be controlled, and the other utilizes the mean arterial pressure. This embodiment utilizing two controllers may provide a better overview of the actual depth of anesthesia.

Using the Hill equation to describe the relationship between the measured effect and the effect-site concentration, four constants ($E_0$, $C_{50}$, $E_{max}$, and γΔ of Equation 1 are estimated for the individual patient. Of these values, the effect at zero plasma drug concentration, $E_0$, is measured as a baseline prior to induction (i.e., at C=0). As can be mathematically proven, for short durations and concentration changes in one direction (e.g., increasing, in the case of induction), it is difficult, if not impossible to make a distinction between ε and $k_{e0}$. Therefore, $k_{e0}$ has been taken out of some literature. See, for example, Billard, Gambus, Chamoun, Stanski and Shafer, "A comparison of Spectral Edge, Delta Power and Bispectral Index as EEG measures of alfentanil, propofol, and midazolam drug effect", *Clinical Pharmacol Ther,* 1997; 61(1) 45–58. Note, however, that more recent research indicates new values for $k_{e0}$. Therefore, $k_{e0}$ may ultimately regain significance.

The other constants ($E_{max}$, $C_{50}$ and γ) can be estimated from the measured values of concentration and effect using a least squares method. Following this approach, the sum of the squared differences between the different measured values and the estimated curve can be minimized such that it becomes possible to reach the best-fitting Hill curve. Through this approach, it is possible to optimize the pharmacokinetic-pharmacodynamic model for the individual patient. Because RUGLOOP is used in one embodiment, preset pharmacokinetic parameters can be used without modification. To account for the pharmacodynamics for an individual patient, the patient-individualized Hill curve can be calculated as discussed above.

One embodiment utilizes RUGLOOP to steer a desired effect-site concentration, corresponding to a certain effect set point preprogrammed by the anesthetist or clinician during the start-up procedure. To reach and maintain the desired effect set point, calculations of the necessary effect-site concentration are done after each measurement of the effect parameters (Bispectral Index and mean arterial pressure). To accomplish this, the invention utilizes the Hill curve measured during the start-up procedure. It is important to note, however, that the individual Hill curve measured during induction is not guaranteed to be valid during surgical or other stimulation.

As illustrated and described above with reference to FIG. 5, a specific chosen target effect value $E_1$ is shown and $P_1$ is the crossing point between the target effect value and the calculated Hill curve. The corresponding actual desired effect-site concentration to achieve $E_1$ is $C_1$. If, due to surgical activities or other outside stimulus, the effect changes to $E_s$, there is a mismatch between the new effect $E_s$ and the desired effect $E_1$ predicted by the effect-site concentration $C_1$. The control methods illustrated in FIGS. 5B and 5C estimate the new required concentration to obtain the desired effect $E_1$ utilizing horizontal or vertical movement of the individual Hill curve derived from the patient as described above.

The first control method, shown in FIG. 5B, assumes that if a measurement of the effect at a particular moment ($E_s$) does not correspond with the effect predicted by the realized concentration and the induction Hill curve at that moment, the desired effect can be reached by increasing the effect-site concentration by the same value as would be necessary to go from the measured effect to the desired effect during the induction. Mathematically, the surgical manipulations or other external stimuli are regarded as shifting the induction Hill curve to the right horizontally to the position at which the current effect-site concentration $C_1$ will produce the measured effect $E_s$. As stated, the shift could be either left or right, causing an increase or decrease in $C_2$ compared to $C_1$ and an effect $E_s$ which may be higher or lower than $E_1$, depending on the direction of the shift. The second control method, illustrated in FIG. 5C, reaches the desired effect by assuming that the actual measured effect lies on the vertically-moved induction curve at the actual effect-site concentration. The new desired concentration can then immediately be read from the moved induction curve at the chosen set point as illustrated in FIG. 5C.

An example implementation utilizes the Bispectral Index and the mean arterial pressure to control the target effect-site concentration with a TCI algorithm according to one embodiment of the invention. In this embodiment, the desired effect-site concentration, the Bispectral Index and the mean arterial pressure can each be used to determine a target effect-site concentration. That is, each of the Bispectral Index and the mean arterial pressure can be independently or jointly used to determine a target effect-site concentration. Both of the values determined by these independent methods can be used to determine a joint target effect-site concentration. In one embodiment, appropriate weighting factors and differential factors can be applied to the values in calculating the joint target effect-site concentration. Additionally, safety limits can be considered as well. The joint target effect-site concentration is used by the RUGLOOP TCI algorithm to calculate the necessary infusion scheme for the anesthetic. These algorithms are used to drive a syringe pump or other device to administer the appropriate medication to patient 116. In one embodiment, the medication administered is the anesthetic Propofol (Diprivan®, Zeneca, Ltd.).

It is important to note that the medication delivery controller 108 may work independently from an increasing or decreasing trend in controlled variables and in the speed of the trend. As a result, the operation of medication delivery controller 108 may cause the actual effect-site concentration to overshoot the desired effect-site concentration, the correction of which may cause unwanted oscillations and instability during anesthesia. To account for this, the embodiment described above can be modified to utilize the difference between two consecutive effect measures, multiplied by a differential factor. The effect-site concentrations can be computed from the effect measures by solving equation 1 for the plasma concentration C; this inverse solution is called the inverse Hill relationship ($C=H^{-1}(E)$). Equation 0 may then be used to calculate the effect-site concentrations corresponding to the values of the effect measures. The differential factor can be chosen by the anesthetist during the start-up procedure. More specifically, in one embodiment, the medication delivery controller can be implemented to calculate:

$$(E_{t_2} - E_{t_1}) * \text{differentialfactor} \qquad (2)$$

As stated, the embodiment described above utilizes both the Bispectral Index and the mean arterial pressure as controlled effect measures. It is useful to choose the relative weighting of the effect-site concentrations calculated using each of these effect measures. After the calculation of the desired effect-site concentration for each controlled effect measure, a weighted mean effect-site concentration is calculated. This mean is used to calculate a new infusion regimen. In one embodiment, the mean is sent to RUGLOOP to be incorporated into the PK algorithm to calculate the new infusion regimen. The weighting of the effect measures can be made by the anesthetist before or during surgery.

Because an overshoot in the administration of Propofol or other anesthetic could be dangerous for the patient, limits and security tools can be implemented according to one embodiment of the invention. In embodiments utilizing the bispectral EEG monitor, the burst suppression ratio can be calculated and utilized as a marker of very deep anesthesia. Suppression ratio, which is a time-domain EEG parameter, indicates the proportion of a given epoch that is represented by an iso-electrical EEG.

In a closed-loop system, a suppression ratio of greater than 10%, for example, can be applied as a limit for the maximum effect-site concentration. If set as a maximum, a further increase in the effect-site concentration is not allowed to be administered even if the medication delivery controller calculates a higher level. In an embodiment implementing Propofol, an effect-site concentration of 10 $\mu$g/mL can be defined as a maximum level to avoid excessive and dangerous Propofol levels. Thus, effect-site concentrations in this embodiment can be limited to that level and an alarm may be produced if that level is reached. The Bispectral Index monitor provides with its information error string codes. These codes can be used to detect artifacts in the processed EEG signal. Then, these actual Bispectral Index numbers can be excluded from further analysis.

In one embodiment incoming controlled variables may be cut off when electromagnetic noise is detected by an artifact detection system in the EEG monitor. An alarm signal is sent to medication delivery controller 108 from sensor packaging 104 indicating that the incoming signals should be ignored in further calculations. When this occurs an audible or visual alarm can also be provided to the anesthetist or user of the system so that they are alerted as to what is occurring. As such, in one embodiment, audible or visual alarms can be provided with sensor package 104 and medication delivery controller 108.

As stated above, other vital parameters can be used in determining changes to be made in the administration of the medication. For example, in an anesthetic application, parameters such as $SpO_2$, $ETCO_2$ and HR can be logged by the processor to monitor safe administration of the medication. Alarms can be provided in order to warn the anesthetist or user of dangerous situations.

As stated above, medication delivery unit 112 can be implemented utilizing a variety of technologies. In one embodiment, a Graseby® 3400 syringe pump is implemented as medication delivery unit 112. This pump is capable of communicating with a controller via an RS-232 interface. Pump infusion rates can be set between 0 and 1200 mL/hour by medication delivery controller 108 in these embodiments. It is important to note that problems with adequate drug administration using syringe pumps can appear when the infusion rates change very frequently; especially in the low rate range. Particularly, with some pumps, the error between the calculated infusion volume and real volume administered increases with increasing rate-change frequency and decreasing average administration rate. Therefore, precautions should be made in the algorithm to decrease the frequency of sending a new calculated pump rate to the syringe pump. For example, instead of sending a new calculated rate to the pump every three seconds, medication delivery controller 108 is set up to send a new calculated pump rate once every ten seconds, yielding a more accurate administration. In this specific example, the ten-second interval is chosen as it is the time range for a new calculation from the pharmacokinetic model algorithm.

In one embodiment, for reasons of safety, the option is provided to the anesthetist to return to open-loop control during administration of the medication. In this mode, the controller remains in a standby mode and the patient's response profile is available if it is desired to return to the closed-loop mode. In the open-loop mode, medication delivery controller 108 can be set to deliver the medication at a specific concentration as set by the user. In one embodiment, even when the administration of medication is canceled or put on hold by the operator, medication delivery controller 108 remains online and continues to calculate the patient's concentration of medication even if no medication is delivered. Therefore, after the operator wishes to cease override, medication delivery controller can again enter the closed-loop mode and restart its action. As such, the medication delivery controller 108 uses the remaining concentration of medication at that moment and calculates how much medication is required to reach and maintain the set point concentration.

The individual Hill curve, calculated at induction, uses a statistical least squares method to compute the best fitting Hill curve around the measured parameters. In one embodiment, medication delivery controller 108 queries the anesthetist or operator whether he or she agrees with the lowest point calculated for the Hill curve. If this lowest value does not make sense the anesthetist or operator, using clinical judgement and experience, can change the value to a lower or higher level. Then, the Hill curve can be recomputed with the new lowest value.

As stated above, in one embodiment the closed loop controller uses the patient individualized pharmacodynamic relation calculated during induction to manage the function of the controller. During closed loop operation, medication delivery controller 108 uses the measured values to calculate a target concentration value for the delivery unit program that will realize the corresponding infusion regimen. A TCI system can be used to reduce the input-output complexity because it allows the blood or effect-site concentration to be targeted instead of the pump infusion rate. As a result, third-order pharmacokinetic behavior of the anesthetic in the body is bypassed. This results in reduced overall order of the system to be controlled and assures better results than using a PID (proportional-integral-derivative) controller to control the infusion rate.

One embodiment utilizes two controllers to minimize the difference between measured and desired effect, while calculating the corresponding effect-site concentration utilizing the patient-specific Hill curve as now described. As discussed above with reference to FIG. 5, in response to external stimulus the effect can be increased from a target value $E_1$ to a new effect $E_s$. As a result, there is a mismatch between the current effect and the desired effect-site concentration. In the embodiment illustrated in FIG. 5B, the desired effect can be reached by increasing the effect-site concentration by the same value as would be necessary to transition from the measured effect $E_s$ to the desired effect $E_1$. This is illustrated by:

$$C_{effect_{t1}} = C_{effect_{t0}} + H^{-1}(\text{desired effect}) - H^{-1}(\text{measured effect}_{t0}) \quad (3)$$

or in terms of FIG. 5B, $$C_2 = C_1 + H^{-1}(E_1) - H^{31\ 1}(E_s)$$

in which $H^{-1}$ stands for the inverse Hill curve relationship and $C_{effect}$ is the concentration at the effect-site. Mathematically, surgical manipulations can be regarded as shifting the induction Hill curve to the right so that the current effect-site concentration predicts the new post-stimulus measured effect.

The second control method illustrated in FIG. 5C states that if a measurement of the effect of a particular moment ($E_s$) does not correspond with the effect ($E_1$) predicted by the realized concentration $C_1$ and the induction Hill curve, the desired effect can be reached by assuming that the actual measured effect lies on the vertically-shifted induction curve at the effect-site concentration. The new desired concentration can then immediately be read from the shifted induction curve $H_s$ at the desired effect. In one embodiment, this can be described as:

$$Ceffect_{t1} = Ceffect_{t0} + H_s^{-1}(H_s(Ceffect_{t0}) - \text{Measured effect}_{t0} + \text{Desired effect}_{t0}) - Ceffect_{t0} = H_s^{-1}(H_s(Ceffect_{t0}) - \text{Measured effect}_{t0} + \text{Desired effect}_{t0}) \quad (4)$$

However, in an alternative embodiment this can be described as:

$$Ceffect_{t1} = Ceffect_{t0} + (Ceffect_{t0} - H_s^{-1}(H_s(Ceffect_{t0}) + \text{Measured effect}_{t0} - \text{Desired effect}_{t0})) \quad (5)$$

or in terms of FIG. 5C:

$$C_2 = C_1 + (C_1 - H_s^{-1}(H_s(C_1) + E_1 - E_s))$$

It is important to note that the closed-loop regulation is essentially integrating because of the patient's body which behaves as an integrator in the loop. Therefore, it is preferred that large proportional factors not be used in the closed-loop because of the risk of instability.

6. Pharmacological Models

Pharmacological models can be used to describe a body's response to the administration of a drug. The pharmacological model is typically split in two parts: the pharmacokinetic behavior of a drug, meaning the relation between the infusion regimen of the drug and the corresponding drug concentration in the blood on one hand, and the pharmacodynamic behavior, which quantifies the relationship between the blood concentration of the drug and its effect.

The pharmacokinetic behavior can be modeled using a $1^{st}$, $2^{nd}$ or $3^{rd}$ order linear differential equation. These equations have a corresponding impulse response, which is in this case the time-course of the blood concentration after a bolus administration of the drug. This impulse response always has the following form for a 3-compartment model:

$$c(t) = A \cdot e^{-at} + B \cdot e^{-bt} + C \cdot e^{-ct} \quad (6)$$

In this equation, one or two coefficients can be zero for a 2- or 1-compartment pharmacokinetic drug model. The curve can be readily computed from blood samples or based on known models.

The presumed linearity of the model yields the advantage that the effect of multiple different simultaneous stimuli equals the sum of the separate effects of the stimuli, in this case multiple bolus doses and/or infusions. This allows TCI systems to keep track of blood concentration using the impulse response c(t) in the following equation for blood concentration C(t) in response to a drug input function over time I(t):

$$C(t) = \int_0^t I(t')c(t-t')dt' \quad (7)$$

Again because of the linearity, the function C(t) can be used inversely in order to calculate the required infusion rate at each moment when targeting a certain blood concentration.

The pharmacodynamic behavior of a drug is usually described using the non-linear Hill curve:

$$E = E_0 - \frac{E_{max}C^\gamma}{C_{50}^\gamma + C^\gamma} \quad (8)$$

In the above equation, y determines the slope of the curve.

For most drugs, a certain time lag is noticed between the time of maximum blood concentration and maximum effect after a bolus infusion. This means the concentration C in the equation cannot be the blood concentration. A (virtual) effect-site compartment and an additional time-constant $k_{e0}$ describing the time lag between blood and effect-site concentration of the drug solve this. The time-lag is described using the following first-order differential equation:

$$\frac{dC_{effect}(t)}{dt} = k_{e0}C_{plasma}(t) - k_{e0}C_{effect}(t) \quad (9)$$

The effect-site compartment is considered small enough not to influence the distribution of the drug in the blood.

The pharmacological drug model parameters can usually be derived using population pharmacological modeling. It can be both practically and economically difficult, if not impossible, to extract all different pharmacological parameters for the specific patient under treatment. There is no guarantee that the specific patient prepared for surgery or drug administration has the same parameters.

Because correct parameters inevitably improve the behavior of the controller, a particular method can be used to determine most possible relevant parameters for the specific patient already prepared for surgery. Then, the patient's reaction to the drug during the induction is monitored. Yet, due to the relatively large half-life of some medications, such as Propofol for example, it is often impractical to bring the patient asleep, awake him or her by lowering the concentration and then increasing the concentration again. This could cause intolerable stress for the patient and take too much time.

As mentioned before, RUGLOOP was used to control the PK aspects of the controller (calculating an infusion rate from a desired effect-site concentration). Because TCI algorithms and three-compartment models are well characterized for most common anesthetic agents, RUGLOOP's PK parameters can be used without changes. Additionally, the Hill equation shows that the absolute value of the blood concentration is not relevant in the case where $C_{50}$ is derived using the same model. This means only the parameters $k_{e0}$, $C_{50}$, $\gamma$, $E_0$ and $E_{max}$ are left to be estimated for the specific patient. It can be proven mathematically that it is not possible to measure both $k_{e0}$ and $\gamma$ using an increasing drug concentration for a short time—that is, relative to the half-life of the product to be infused. For example consider a stepwise increase in plasma concentration. The effect-site concentration follows as:

$$c_{effect} = c_{plasma}(1 - e^{-k_{e0}t}) \quad (10)$$

The Hill curve then gives the related effect:

$$effect = E_0 - E_{max}\frac{C_{effect}^\gamma}{C_0^\gamma + C_{effect}^\gamma} \quad (11)$$

$$effect = E_0 - \frac{E_{max}C_{plasma}^\gamma(1-e^{-k_{e0}t})^\gamma}{C_0^\gamma + C_{plasma}^\gamma(1-e^{-k_{e0}t})^\gamma} \quad (12)$$

Series expansion of $$(1 - e^{-k_{e0}t})$$

for small $k_{e0}t$ yields $k_{e0}t$ which makes:

$$effect = E_0 - \frac{E_{max}C_{plasma}^\gamma(k_{e0}t)^\gamma}{C_0^\gamma + C_{plasma}^\gamma(k_{e0}t)^\gamma} \quad (13)$$

7. Software Embodiments

Figure 9:
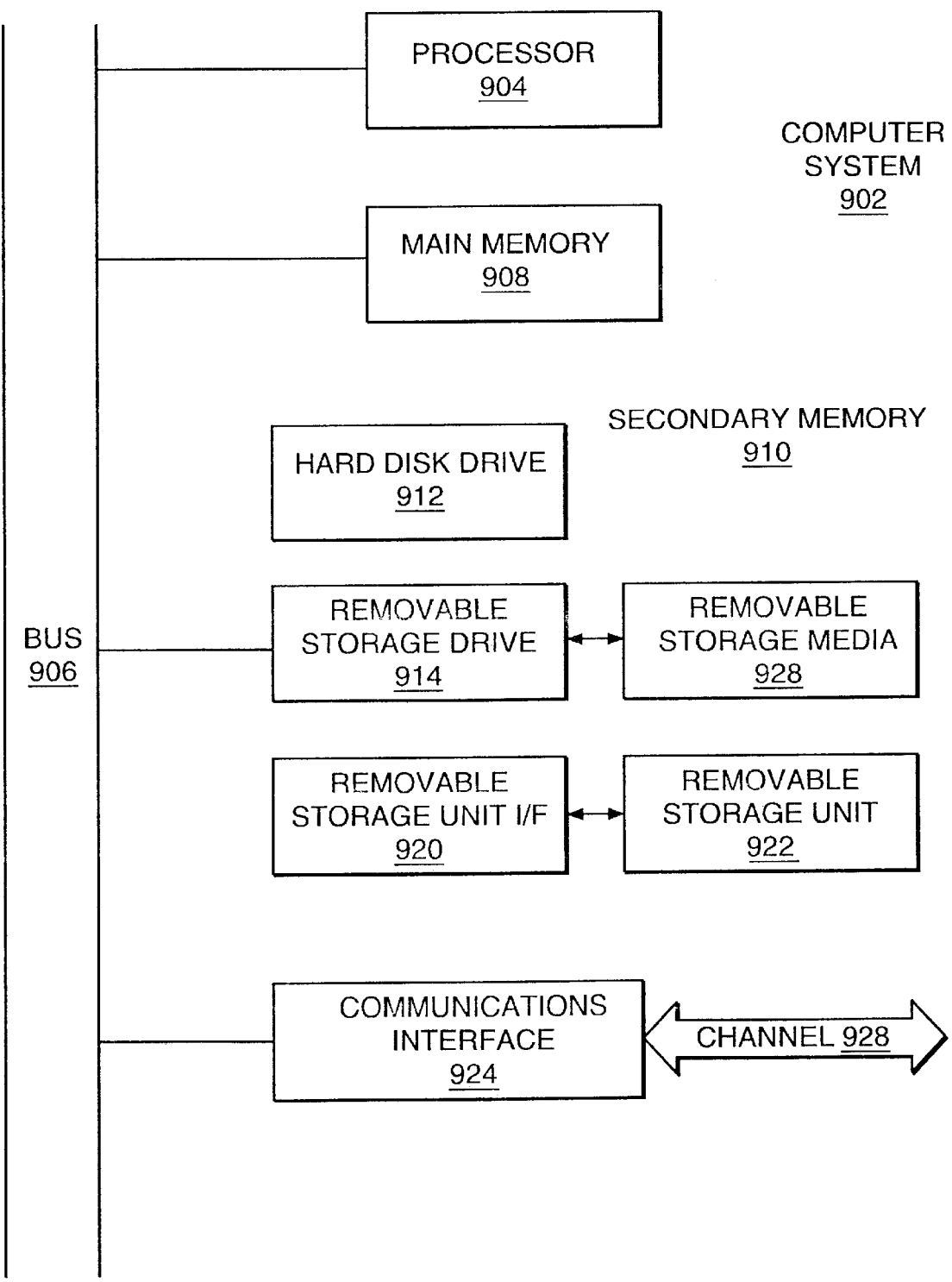
FIG. 9 is a block diagram illustrating an example architecture of a computer system which can be used to implement the functionality of the invention in accordance with one embodiment.

The various components of the invention can be implemented using hardware, software or a combination of both. FIG. 9 is a block diagram illustrating a general-purpose computer system, including examples of computer readable media for providing computer software or instructions to perform the functionality described herein. The illustrated computer system 902 includes one or more processors, such as processor 904. The processor 904 is connected to a communication bus 906. Various software embodiments are described in terms of this example computer system. After reading this description, it will become apparent to a person of ordinary skill in the relevant art how to implement the invention using other computer systems or computer architectures, including, for example, the architectures or portions of the architectures illustrated in FIGS. 1, 6 and 8.

Computer system 902 also includes a main memory 908, preferably Random Access Memory (RAM), and can also include a secondary memory 910. The secondary memory 910 can include, for example, a hard disk drive 912 and/or a removable storage drive 914, representing a floppy disk drive, a magnetic tape drive, an optical disk drive, etc. Removable storage drive 914 reads from and/or writes to removable storage media 928. Removable storage media 928, represents a floppy disk, magnetic tape, optical disk, etc., which is read by and written to by removable storage drive 914. As will be appreciated, the removable storage media 928 includes a computer-usable storage medium having therein computer software and/or data.

In alternative embodiments, secondary memory 910 includes other similar means for allowing computer programs or other instructions to be loaded into computer system 902. Such means can include, for example, a removable storage unit 922 and a removable storage unit interface 920. Examples of such can include a program cartridge and cartridge interface (such as, for example, that found in video game devices), a removable memory chip (such as, for example, an EPROM, PROM or other memory device) and associated socket, and other removable storage units 922 and removable storage unit interfaces 920 which allow software and data to be transferred from the removable storage unit 922 to computer system 902. In some embodiments, removable storage unit 922 may be affixed permanently to removable storage unit interface 920.

Computer system 902 can also include a communications interface 924. Communications interface 924 allows software and data to be transferred between computer system 902 and external devices. Examples of communications interface 924 can include a modem, a network interface (such as an Ethernet card), a communications port, a PCMCIA slot and card, etc. Software and data transferred via communications interface 924 are in the form of signals which can be electronic, electromagnetic, optical or other signals capable of being received by communications interface 924. These signals are provided to communications interface 924 via a channel 928. This channel 928 carries signals and can be implemented using a wireless medium, wire or cable, fiber optics, or other communications medium. Some examples of a channel can include a phone line, a cellular phone link, an RF link, a network, the Internet, and other communications channels.

In this document, the terms "computer program medium" and "computer usable medium" are used to generally refer to media such as removable storage media 928, a hard disk installed in hard disk drive 912, removable storage unit 922 and signals on channel 928. These terms can also refer to main memory 908 where main memory 908 stores a computer program or a part thereof. These computer program products are means for providing software to computer system 902.

Computer programs or instructions (also called computer control logic) can be stored in main memory 908 and/or secondary memory 910. Computer programs can also be received via communications interface 924. Such computer programs, when executed, enable the computer system 902 to perform the features of the present invention as discussed herein. In particular, the computer programs, when executed, enable the processor 904 to perform the features of the present invitation. Accordingly, such computer programs represent controllers of the computer system 902.

In an embodiment where the elements are implemented using software, the software may be stored in a computer program product and loaded into computer system 902 using removable storage drive 914, removable storage unit 922, and hard drive 912 or communications interface 924. The control logic (software), when executed by the processor 904, causes the processor 904 to perform the functions of the invention as described herein.

In another embodiment, the elements are implemented primarily in hardware using, for example, hardware components such as Application Specific Integrated Circuits (ASICs). Implementation of the hardware state machine so as to perform the functions described herein will be apparent to persons of ordinary skill in the relevant art(s). Although not a "computer program" in the traditional sense, the hardware components can be thought of as a computer program medium (albeit, perhaps hard-wired) which enables the system to perform the described functions. In yet another embodiment, elements are implemented using a combination of both hardware and software. In this embodiment, the combination of the hardware and software can likewise be thought of as a computer program medium that enables the system to perform the described functions.

8. Conclusion

While various embodiments of the present invention have been described above, it should be understood that they have been presented by way of example only, and not limitation. Thus, the breadth and scope of the present invention should not be limited by any of the above-described exemplary embodiments, but should be defined only in accordance with the following claims and their equivalents.

What is claimed is:

1. A method for controlling the administration of medication to a patient to achieve and maintain a desired effect in said patient, the method comprising the steps of:

computing a first patient response profile, said patient response profile indicating the patient's individualized response to said medication;

using the first patient response profile to determine a first concentration level of said medication to maintain said target effect in said patient;

determining whether the patient's response to said first concentration level of said medication has changed;

computing a second patient response profile reflecting the patient's new individualized response to said medication; and using said second patient response profile to determine a new concentration level of medication to maintain said target effect in said patient.

2. The method of claim 1, further comprising the step of controlling a medication delivery unit to deliver said medication to said patient to achieve said determined concentration level of medication.

3. The method of claim 2, wherein said concentration level of medication is a blood concentration level.

4. The method of claim 2, wherein said concentration level of medication is an effect-site concentration level.

5. The method of claim 1, wherein said step of computing said first patient response profile comprises the steps of:

delivering a first concentration level of medication to the patient;

determining an effect on the patient of said first concentration level of medication delivered to the patient;

delivering one or more increased concentration levels of medication to the patient;

determining an effect on the patient of said one or more increased concentration levels of medication delivered to the patient; and calculating said patient response profile based on said effect of said medication on the patient.

6. The method of claim 5, wherein said steps of delivering said concentration levels of medication to the patient comprise the step of controlling a medication delivery unit to deliver medication to the patient at a rate determined to achieve said concentration levels.

7. The method of claim 6, wherein said medication delivery unit comprises at least one of the group of an infusion pump and an inhalation delivery device.

8. The method of claim 1, wherein said steps of determining an effect on the patient of said concentration levels of medication comprises the steps of:

sensing one or more attributes of the patient to determine one or more parameters indicating the patient's state;

using at least one of said one or more parameters to determine the effect of said concentration level of said medication on said patient.

9. The method of claim 8, wherein said one or more parameters comprise a Bispectral Index related to an EEG of the patient and the patient's mean arterial pressure.

10. The method of claim 8, wherein said one or more parameters comprise at least one of the group of blood pressure, heart rate, temperature and EEG parameters.

11. The method of claim 1, wherein said step of determining whether the patient's response to said first concentration level of medication has changed comprises the step of measuring the effect of said first concentration level of medication on said patient and comparing said measured effect to the target effect defined by said patient response profile for said first concentration level.

12. The method of claim 1, wherein said step of computing a second patient response profile comprises the steps of:

determining an operating point representing a measured effect of said first concentration level of medication on said patient; and shifting said first patient response profile until said patient response profile intersects said operating point.

13. The method of claim 12, wherein said step of shifting said first patient response profile comprises the step of shifting said first patient response profile vertically or horizontally until said patient response profile intersects said operating point.

* * * * *